US00PP31994P2

(12) United States Plant Patent
Bronsther

(10) Patent No.: US PP31,994 P2
(45) Date of Patent: Jul. 21, 2020

(54) ***JUNIPERUS* PLANT NAMED 'RIKAG'**

(50) Latin Name: *Juniperus chinensis*
Varietal Denomination: RIKAG

(71) Applicant: Rika Bronsther, Franklin Square, NY (US)

(72) Inventor: Rika Bronsther, Franklin Square, NY (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,153

(22) Filed: Feb. 26, 2019

(51) Int. Cl.
*A01H 5/00* (2018.01)
*A01H 7/00* (2006.01)

(52) U.S. Cl.
USPC ..... Plt./214

(58) Field of Classification Search
USPC ..... Plt./214
See application file for complete search history.

*Primary Examiner* — Susan McCormick Ewoldt
(74) *Attorney, Agent, or Firm* — Cassandra Bright

(57) ABSTRACT

A new and distinct *Juniperus* cultivar named 'RIKAG' is disclosed, characterized by abundant fruit production and dense foliage. The new cultivar is a *Juniperus chinensis*, suitable for ornamental garden purposes.

2 Drawing Sheets

Latin name of the genus and species: *Juniperus chinensis*.
Variety denomination: 'RIKAG'.

BACKGROUND OF THE INVENTION

The new cultivar is a product of a naturally occurring mutation. This new variety, hereinafter referred to as 'RIKAG', was selected as a single branch mutation of an unnamed, unpatented *Juniperus chinensis*. The new variety was discovered by the inventor Rika Bronsther in a commercial nursery in Hemstead, N.Y. during Spring of 2006.

After identifying the new variety as a potentially interesting selection, semi-hardwood cuttings were taken at the same nursery in Hemstead, N.Y., then taken to a commercial nursery in Grand Haven, Mich. for rooting in the Spring of 2006. Confidential, controlled testing and propagation, was conducted to assess the stability of the unique characteristics of this variety. At least four generations have been reproduced and have shown that the unique features of this cultivar are stable and reproduced true to type. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'RIKAG' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RIKAG' These characteristics in combination distinguish 'RIKAG' as a new and distinct *Juniperus* cultivar:

1. Abundant fruit production.
2. Dense foliage.

COMPARISON TO PARENT VARIETY

'RIKAG' is similar in most horticultural characteristics to the parent variety. Plants of the new cultivar 'RIKAG' however, differ in the following:

1. The new variety has dense green foliage, while parent has less dense and darker green foliage.
2. The new variety produces more fruit than the parent.

COMMERCIAL COMPARISON

In addition to the parent, 'RIKAG' can be compared to the commercial variety *Juniperus chinensis* 'Hetzi Columnaris', unpatented. The varieties are similar in most horticultural characteristics, however, plants of 'RIKAG' differ in the following:

1. New cultivar has bright green foliage with a tinge of gold; comparator has darker green foliage with a bit of grey.
2. Plants of the new variety are larger in diameter than this comparator.
3. New variety produces blue fruit, while comparator produces blue-purple fruit.

BRIEF DESCRIPTION OF THE PHOTOGRAPHS

Figure 1:
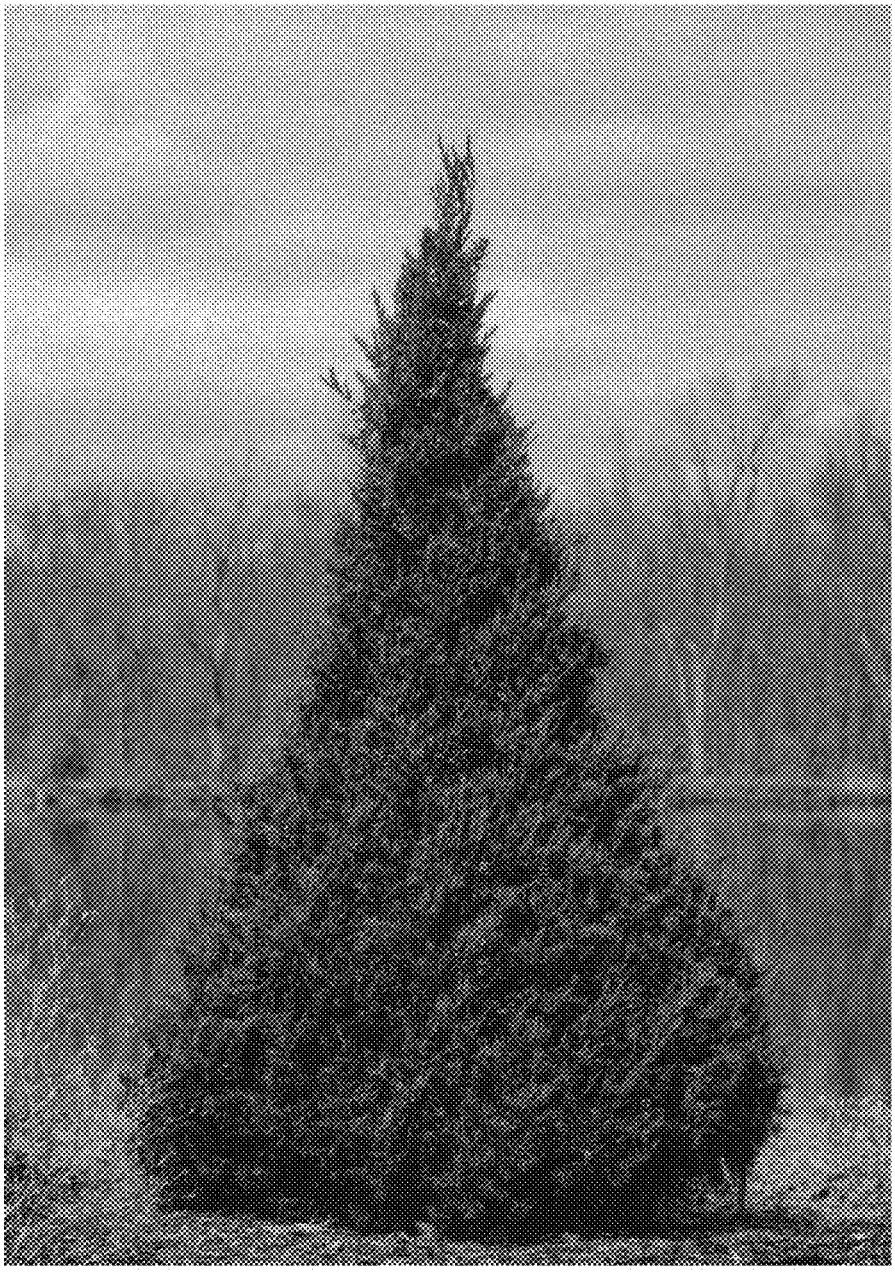

The accompanying photograph in FIG. 1 illustrates in full color a typical plant of 'RIKAG' grown outdoors in Grand Haven, Mich. The plant is approximately 7 years old, and is shown in the ground at a testing plot.

Figure 2:
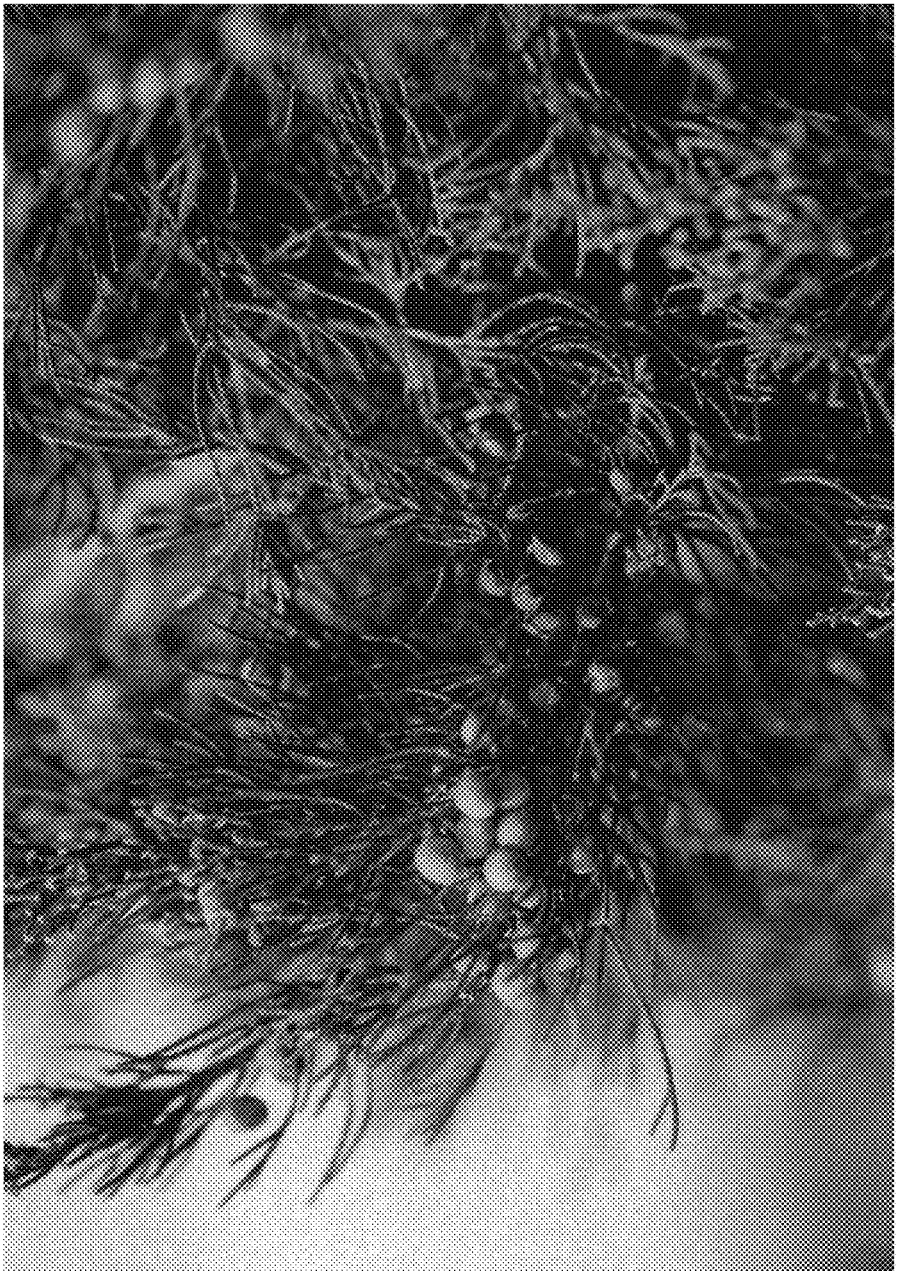

FIG. 2 illustrates a close up of a branch of the new variety, with fruits.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'RIKAG' plants grown outdoors in Grand Haven, Mich. Plants are approximately 1-2 years old, in a 3 gallon size container. Measurements and numerical values represent averages of typical plant types.

Botanical classification: *Juniperus chinensis* 'RIKAG'.

Propagation:

*Time to rooting.*—90 days at approximately 24° F.

*Time to produce a rooted cutting.*—Approximately 200 days.

*Root description.*—Fibrous, thick to thin, moderately dense, moderately branched. Colored brown and white, not accurately measured by R.H.S. chart.

Plant:

*Growth habit.*—Upright and outward.

*Height.*—45 cm.

*Plant spread.*—17 cm.

*Typical growth rate.*—Rapid, filling a one gallon pot in a single season.

*Branching characteristics.*—Approximately 15 to 20 lateral branches. Lateral stems are held at an angle of approximately 10 to 80 degree from the main stem.

*Stems.*—Length: Average 15 to 18 cm. Diameter: 0.7 cm. Color: New growth: RHS Green 141D. Mature growth: RHS Greyed-Orange 166A. Appearance: Round with scales. Strength: Strong.

*Lateral branches.*—Length: 12.5 cm. Diameter: 5 mm. Shape in cross section: Round. Strength: Strong.

*Internode length.*—1 cm.

Foliage:

*General description.*—Needle-like, imbricate, slightly appressed.

*Leaf.*—Arrangement: Alternate. Type: Simple, needle-like. Shape of blade: Linear. Average Length: 7.5 mm. Average Width: 1 mm. Apex: Acute. Base: Truncate. Margin: Entire. Texture of top surface: Smooth. Texture of bottom surface: Smooth. Color: Young foliage upper side: Near RHS Green 138A, tinged Yellow-Green 151A. Apex Greyed-Orange 163B. Young foliage under side: Near RHS Green 138A, tinged Yellow-Green 151A. Apex Greyed-Orange 163B. Mature foliage upper side: Near RHS Green 138A, tinged Yellow-Green 153D. Mature foliage under side: Near RHS Green 138A, tinged Yellow-Green 153D. Venation: Linear, indistinguishable from leaf blade.

*Petiole.*—Length: 2 mm. Diameter: 1 mm. Texture, upper side: Smooth. Texture, under side: Smooth. Color, upper side: Near RHS Green 138A. Color, under side: Near RHS Green 138A.

Flower: Flowering not observed.

Fruit:

*Size.*—About 10 mm in length and 7.5 mm in diameter.

*Shape.*—Globular.

*Quantity.*—30 to 50 per lateral branch.

*Color.*—Near RHS Blue 103A at maturity. Immature fruits near RHS Yellow-White 158A flushed Greyed-Yellow 161B.

*Texture.*—Slightly rough, dry.

*Seeds.*—3 per fruit, 5 mm long, 4 mm wide. Colored near RHS Greyed-Orange 175C.

Other characteristics:

*Disease and pest resistance.*—Neither resistance nor susceptibility observed.

*Drought tolerance.*—No tolerance for drought.

*Temperature tolerance.*—USDA Zones 3-9.

What is claimed is:

1. A new and distinct cultivar of *Juniperus* plant named 'RIKAG' as herein illustrated and described.

* * * * *